United States Patent [19]

Freimuth et al.

[11] 4,166,067

[45] Aug. 28, 1979

[54] PROCESS FOR THE PREPARATION OF ALKOXYMETHYL-ISOCYANATES

[75] Inventors: Reinhard Freimuth, Bergisch-Gladbach; Kuno Wagner, Leverkusen; Kurt Findeisen, Odenthal; Klaus König, Leverkusen; Peter Heitkämper, Dormagen, all of Fed. Rep. of Germany

[73] Assignee: Bayer Aktiengesellschaft, Leverkusen, Fed. Rep. of Germany

[21] Appl. No.: 947,916

[22] Filed: Oct. 2, 1978

[30] Foreign Application Priority Data

Oct. 19, 1977 [DE] Fed. Rep. of Germany ....... 2746963

[51] Int. Cl.² .................................... C07C 118/00
[52] U.S. Cl. ........................ 260/453 P; 260/453 AL
[58] Field of Search ........................... 260/453 P

[56] References Cited

U.S. PATENT DOCUMENTS

| 3,379,749 | 4/1968 | Hennig et al. | 260/453 P |
| 3,898,259 | 8/1975 | Hearsey | 260/453 P |

*Primary Examiner*—Dolph H. Torrence
*Attorney, Agent, or Firm*—Gene Harsh; Lawrence S. Pope

[57] ABSTRACT

This disclosure relates to a process for the preparation of alkoxymethylisocyanates by reacting alkoxylmethyl tri-substituted ureas with isocyanates which have higher boiling points than the alkoxy methyl isocyanates produced. The process is also applicable to alkenoxy methyl tri-substituted ureas to make the corresponding isocyanates. Ureas of commercial purity may be used to obtain good yields of isocyanate when between about 0.03 and 0.2 mol of carbodiimide groups are present per mol of urea group. The carbodiimide containing compounds may also carry free isocyanate groups, in which case they should have a boiling point above that of the isocyanate product.

8 Claims, No Drawings

PROCESS FOR THE PREPARATION OF ALKOXYMETHYL-ISOCYANATES

FIELD OF THE INVENTION

This invention relates to a new process for the preparation of saturated or olefinically unsaturated alkoxymethylisocyanates.

BACKGROUND OF THE INVENTION

Alkoxymethylisocyanates are known, in particular methoxymethylisocyanate (MMI). These compounds are interesting intermediate products for the production of lacquer binders which are capable of being cross-linked (see e.g. German Pat. Nos. 1,244,410; 1,619,238; 1,911,180 and 1,644,801 and German Offenlegungsschrift Nos. 1,570,578; 1,595,701 and 1,644,815).

In spite of the excellent lacquer technical properties of the binders described in the above literature, alkoxymethylisocyanate derivatives have not so far become established in practice because no technically completely satisfactory method has yet been disclosed for producing alkoxymethylisocyanates. The known method of producing alkoxymethylisocyanates, in particular methoxymethylisocyanate (see e.g. German Auslegeschrift No. 1,205,087) by the reaction of alkylchloromethyl ethers, in particular chloromethyl-methyl ethers with sodium cyanate, has the disadvantage that the chloromethyl ether used as starting material is a substance which, manufactured on a large technical scale, is invariably contaminated with physiologically very harmful substances (bis-(chloromethyl)-ether), with the result that the known method of producing alkoxymethylisocyanates, in particular methoxymethylisocyanate, cannot be employed on a large technical scale.

It was therefore an object of the present invention to provide a new process for the preparation of alkoxymethylisocyanates, in particular of methoxymethylisocyanate, which may also be carried out on a large technical scale. The problem may be solved by the process according to the present invention which is described below.

SUMMARY OF THE INVENTION

The present invention relates to a process for the preparation of isocyanates corresponding to the following general formula:

R—O—CH$_2$—NCO characterized in that tri-substituted ureas corresponding to the following general formula:

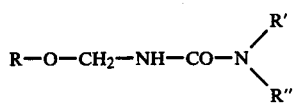

are reacted at temperatures of from 50° to 250° C. with organic mono- or polyisocyanates which have a higher boiling point than the products of the process. In the above general formulae, R represents a saturated aliphatic hydrocarbon group having from 1 to 4 carbon atoms or an allyl group; and R' and R" independently represent organic groups which are inert under the reaction conditions, and the groups R' and R", together with the nitrogen atom of the urea group, may also form a heterocyclic ring.

DETAILED DESCRIPTION OF THE INVENTION

Particularly preferred tri-substituted ureas to be used as starting material for the process according to the present invention are those corresponding to the above general formula wherein R represents a methyl group.

The nature of the substituents R' and R" is completely unimportant in determining whether the process according to the present invention may be carried out. These substituents are generally straight- or branched-chain alkyl or alkenyl groups optionally substituted by halogen atoms or by nitrile, aryl or lower alkoxy groups; cycloalkyl or cycloalkenyl groups optionally substituted by halogen or by lower alkyl or alkoxy groups; or aryl groups having up to 16 carbon atoms optionally substituted by halogen or by nitro, nitrile, carbalkoxy, carbonyl, lower alkyl, alkenyl, alkoxy, or aralkyl groups.

Most preferably, the groups R' and R" are derived from the corresponding simple secondary amines corresponding to the following general formula:

This means that the groups R' and R" are most preferably alkyl groups having from 1 to 6 carbon atoms which may be unsaturated or may, together with the nitrogen atom, form a saturated heterocyclic ring optionally containing an ether oxygen atom.

Typical examples of the preferred tri-substituted ureas to be used in the process according to the present invention are thus N-methoxymethyl-N',N'-dimethyl urea; N-methoxymethyl-N',N'-diethyl urea; N-butoxymethyl-N',N'-diisopropyl urea; N-butoxymethyl-N',N'-dicyclohexyl urea, N-butoxymethyl-N',N'-diallyl urea and N-(methoxymethylaminocarbonyl)-piperidine or -p-morpholine.

The above mentioned starting compounds for the process according to the present invention may be prepared by processes known in the art of reacting the corresponding di-substituted ureas

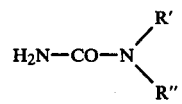

(prepared, e.g., from the corresponding secondary amine, phosgene and ammonia) with formaldehyde and then etherifying the resulting N-methylol-substituted urea corresponding to the following general formula:

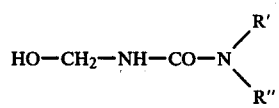

with alcohols corresponding to the following general formula:

R—OH

The principle of this method of synthesis has been described, for example, in Annalen der Chemie 361, 133, 135 (1908); berichte der Deutschen Chemischen Gesellschaft 41, 24 (1908); J. of the Chem. Society of Japan 11/3/, 248 (1936) and in U.S. Pat. No. 3,125,601.

The process according to the present invention is carried out in the presence of any organic compounds which contain isocyanate groups, but are otherwise inert and which have higher boiling points than the products obtained by the process according to the present invention. The difference in boiling points should be at least sufficient to ensure clear separation of the products of the process by distillation from the isocyanates used as auxiliary agents. This difference in boiling points is generally at least 10° C. at 1 mbar. The higher boiling isocyanates used as auxiliary agents are preferably used in such quantities that the reaction mixture contains at least one, preferably from about 1 to 20, most preferably from about 1 to 10, especially from about 2 to 6 equivalents of isocyanate groups of the auxiliary isocyanate per mol of tri-substituted urea.

Provided this condition concerning the difference in boiling points is fulfilled, any isocyanates or polyisocyanates conforming to the above definition may be used for the process according to the present invention. This means, in particular, that any aliphatic, cycloaliphatic, araliphatic, aromatic or heterocyclic monoisocyanates or polyisocyanates may be used. The following are examples of monoisocyanates which may be used: 6-chlorohexyl isocyanate, dodecyl isocyanate, tetradecyl isocyanate, hexadecyl isocyanate, octadecyl isocyanate, stearyl isocyanate, 4-chlorocyclohexyl isocyanate, 4-chlorophenyl isocyanate, 3,4-dichlorophenyl isocyanate, 2-nitrophenyl isocyanate, 4-nitrophenyl isocyanate, 3-chloro-p-tolyl isocyanate, and 1-naphthyl isocyanate. The following are examples of suitable polyisocyanates: ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3- and 1,4-diisocyanate and mixtures of these isomers, 1-isocyanato-3,3,5-trimethyl-5-isocyanatomethylcyclohexane (German Auslegeschrift No. 1,202,785), hexahydrotolylene-2,4- and 2,6-diisocyanate and mixtures of these isomers, hexahydrophenylene-1,3- and/or -1,4-diisocyanate, perhydrodiphenylmethane-2,4'- and/or -4,4'-diisocyanate, phenylene-1,3- and -1,4-diisocyanate, tolylene-2,4- and -2,6-diisocyanate and mixtures of these isomers, diphenylmethane-2,4'- and/or -4,4'-diisocyanate, naphthylene-1,5-diisocyanate triphenylmethane-4,4',4''-triisocyanate, polyphenyl-polymethylene polyisocyanates which may be obtained by aniline/formaldehyde condensation followed by phosgenation, e.g. those described in British Pat. Nos. 874,430 and 848,671, perchlorinated aryl polyisocyanates, e.g. those described in German Auslegeschrift No. 1,157,601, the diisocyanates described in U.S. Pat. No. 3,492,330, polyisocyanates containing allophanate groups, such as those described, e.g. in British Pat. No. 944,890, Belgian Pat. No. 761,626 and published Dutch Pat. Application No. 7,102,524, polyisocyanates containing isocyanurate groups, e.g. as described in German Pat. Nos. 1,022,789; 1,222,067 and 1,027,394 and in German Offenlegungsschrift Nos. 1,929,034 and 2,004,048, polyisocyanates containing urethane groups, e.g. as described in Belgian Pat. No. 752,261 or in U.S. Pat. No. 3,394,164, polyisocyanates containing acylated urea groups according to German Pat. No. 1,230,778, polyisocyanates containing biuret groups as described, e.g. in German Pat. No. 1,101,394, British Pat. No. 889,050 and French Pat. No. 7,017,514, polyisocyanates prepared by telomerization reactions as described, e.g. in Belgian Pat. No. 723,640, polyisocyanates containing ester groups as described, e.g. in British Pat. Nos. 956,474, and 1,072,956, U.S. Pat. No. 3,567,764 and German Pat. No. 1,231,688 and reaction products of the above-mentioned isocyanates with acetals according to German Pat. No. 1,072,385.

The distillation residues containing isocyanate groups from the commercial production of isocyanates may also be used, optionally dissolved in one or more of the above-mentioned mono- or poly-isocyanates. Mixtures of the above-mentioned mono- or poly-isocyanates may also be used.

As a rule, it is particularly preferred to use chlorohexyl isocyanate and commercially readily available polyisocyanates, such as hexamethylene diisocyanate, isophorone diisocyanate, tolylene-2,4- and 2,6-diisocyanate and mixtures of these isomers ("TDI"), polyphenyl-polymethylene polyisocyanates obtained by aniline/formaldehyde condensation followed by phosgenation ("crude MDI") and polyisocyanates containing urethane groups, allophanate groups, isocyanurate groups, urea groups or biuret groups ("modified polyisocyanates").

The process according to the present invention is carried out by heating a mixture of the tri-substituted ureas with the auxiliary isocyanate at from about 50° to 250° C., preferably from about 60° to 160° C., more particularly from about 80° to 130° C., at a pressure of from ab-ut 0.1 to 1013 mbar (normal pressure), preferably from about 1 to 400 mbar, optionally in the presence of an auxiliary solvent, such as chlorobenzene, dichlorobenzene, trichlorobenzene, dioxane, benzene, toluene, xylene, diphenyl ether or sulpholane. The reaction is generally carried out in the absence of solvents.

The products according to the present invention may generally be obtained from the reaction mixtures by distillation under the given conditions of temperature and pressure.

According to a preferred embodiment of the process according to the present invention, the reaction between tri-substituted ureas and auxiliary isocyanates is carried out in the presence of organic compounds which have carbodimide groups. The use of such organic compounds containing carbodiimide groups not only results in considerable improvements in yields, but also enables very impure tri-substituted ureas which are obtained as commercial products from the above-mentioned methods of preparation to be used without further purification.

The carbodiimides used according to the present invention may be any organic compounds which contain carbodiimide groups, in particular aliphatic, cycloaliphatic, araliphatic or aromatic mono- or poly-carbodiimides, provided they contain no other groups liable to interfere with the progress of the reaction, for example isocyanate-reactive groups.

Such organic compounds containing carbodiimide groups are prepared by the known method of carbodiimidization of organic mono- or poly-isocyanates of the type exemplified above.

Suitable carbodiimides include, for example, the carbodiimidization products of monoisocyanates of the type exemplified above, e.g. diethyl carbodiimide, dipropyl carbodiimide, di-iso-propyl carbodiimide, dibutyl carbodiimide, dicyclohexyl carbodiimide, di-2-methyl-cyclohexyl carbodiimide, diphenyl carbodiimide and the oligocarbodiimidization products of diisocyanates, such as hexamethylene diisocyanate, 2,4-diisocyanatotoluene, 4,4'-diisocyanatodiphenylmethane or 3,3,5-trimethyl-5-isocyanatomethyl-cyclohexyl isocyanate having a degree of oligomerization of from about 2 to 15 (oligocarbodiimide having from about 2 to 15 carbodiimide groups).

The carbodiimides are preferably used in such quantities in the process according to the present invention that the reaction mixture contains from about 0.02 to 0.4, preferably from about 0.03 to 0.2, mol of carbodiimide groups: —N=C=N—, per urea group:

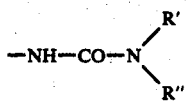

Depending on the size of the inert groups both in the urea used as starting material and in the carbodiimides, this corresponds to a quantity of from ca. 3 to 50, preferably from about 5 to 20%, by weight, of carbodiimide, based on the quantity of tri-substituted urea put into the process.

If the organic compounds containing carbodiimide groups in addition contain free isocyanate groups (carbodiimidization products of di- and/or poly-isocyanates), the auxiliary isocyanates exemplified above may be partly or completely dispensed with because in such cases the free isocyanate groups of the carbodiimides take over the function of the auxiliary isocyanates. In that case, all that is necessary, in order to prevent a loss in yields, is to ensure that the total quantity of isocyanate groups present in the reaction mixture conforms to the particulars give above and that the carbodiimide which contains isocyanate groups has a boiling point at least 10 deg. cent. higher than the product of the process, a condition which in the case of polyisocyanates containing carbodiimide groups is in any case fulfilled since these are generally substances which cannot be distilled.

When such organic compounds which contain carbodiimide groups are used, the process according to the present invention is preferably carried out by adding the carbodiimide to the tri-substituted urea which is to be decomposed and then adding the higher boiling mono- or di-isocyanate and isolating the isocyanate produced according to the present invention or using the reaction mixture directly for an isocyanate polyaddition reaction.

For example, hexamethylene diisocyanate is added at 100° C. and at a reduced pressure to a mixture of N,N-dimethyl-N'-methoxymethyl- urea and diphenyl carbodiimide which has been left to stand for some time at 50° C. and the mixture is left for some time at 120° C. before the methoxymethyl isocyanate is isolated in a cooled receiver.

The process according to the present invention may be used for the preparation of alkoxymethyl isocyanates, in particular methoxymethyl isocyanate, for which no technically completely satisfactory method of production has hitherto been available.

EXAMPLES

EXAMPLE 1

132 g (1 mol) of a technical grade (purity<98%) N,N-dimethyl-N'-methoxymethyl-urea and 13 g of diphenyl carbodiimide are together heated to 50° C. for 2 hours. After the addition of 504 g (3 mol) of hexamethylene diisocyanate, 80 g (91%) of methoxymethyl isocyanate are obtained in the cooled receiver after 2 hours at from 80° to 120° C. under a reduced pressure of 20 mbar.

COMPARISON EXAMPLE

When the process is carried out as in Example 1, but without the addition of carbodiimide, methoxymethyl isocyanate is isolated only in traces, obviously due to the considerable quantities of impurities in the urea derivative put into the process.

EXAMPLE 2

160 g (1 mol) of a technical grade (purity<98%) N,N-diethyl-N'-methoxymethyl urea and 16 g of diphenyl carbodiimide are heated to 50° C. for 2 hours. After the addition of 504 g (3 mol) of hexamethylene diisocyanate, 76.5 g (88%) of methoxymethyl isocyanate are obtained in the cooled receiver after 2 hours at from 80° to 120° C. under a reduced pressure of 20 mbar.

COMPARISON EXAMPLE

When the process is carried out as in Example 2, but without the addition of carbodiimide, methoxymethyl isocyanate is isolated only in traces, obviously due to the considerable quantities of impurities in the urea derivative put into the process.

EXAMPLE 3

When the process is carried out analogously to Example 1, i.e., using the same equivalent ratio of urea to auxiliary isocyanate, butoxymethyl isocyanate is obtained in 85% yield from a technical grade (purity<98%) N,N-dicyclohexyl-N'-butoxymethyl urea and 13%, by weight, of dicyclohexyl carbodiimide, based on the quantity of urea, at from 90° to 120° C. when an 80:20 mixture of 2,4- and 2,6-tolylene diisocyanate is used.

EXAMPLE 4

When the process is carried out analogously to Example 1, i.e., using the same equivalent ratio of urea to auxiliary isocyanate, propoxymethyl isocyanate is obtained in a yield of 86%, measured in terms of the isocyanate content when a technical grade (purity<98%) N-phenyl-N-methyl-N'-propoxymethyl urea is reacted with 15%, by weight, based on the quantity of urea, of di-2,3-dichlorophenyl-carbodiimide at from 100° to 130° C. with the addition of a polyisocyanate mixture of the diphenyl methane series.

EXAMPLE 5

When the process is carried out analogously to Example 1, i.e., using the same equivalent ratio of urea to auxiliary isocyanate, i-butoxymethyl isocyanate is obtained in 84% yield, based on the isocyanate content, from a technical grade (purity<98%)N-benzyl-N-phenyl-N'-butoxymethyl urea with 15%, by weight, based on the quantity of urea, of di-2,3-dichlorophenyl carbodiimide at from 100° to 130° C., using a polyisocyanate mixture of the diphenyl methane series.

EXAMPLE 6

Carrying out the process analogously to Example 1, i.e., using the same equivalent ratio of urea to auxiliary isocyanate, butoxymethyl isocyanate is obtained in 86% yield from a technical grade (purity <98%) N,N-dihexahydrobenzyl-N'-butoxymethyl urea and 15%, by weight, based on the quantity of urea, of di-2,4-dichloro-phenyl carbodiimide at from 90° to 120° C., using 6-chlorohexyl isocyanate.

EXAMPLE 7

By a process analogous to that of Example 1, i.e., using the same equivalent ratio of urea of auxiliary isocyanate, butoxymethyl isocyanate is obtained in 86% yield from a technical grade (purity <98%)N,N-diallyl-N'-butoxymethyl urea and 15%, by weight, based on the quantity of urea, of di-2,4-dichlorophenyl carbodiimide at from 90° to 120° C., using 6-chlorohexyl isocyanate.

EXAMPLE 8

202 g (1 mol) of a technical grade (purity <98%) N,N-diethyl-N'-butoxymethyl urea are mixed at 60° C. with 600 g of a diisocyanato carbodiimide which has been obtained by carbodiimidization of hexamethylene diisocyanate and has an isocyanate content of 20%, by weight, (see Angewandte Chemie 74, 801 (1962)). The mixture is then heated to from 100° to 130° C. at a pressure of 20 mbar and the butoxymethyl isocyanate formed begins to distill off. 104 g (81%) of the monoisocyanate are obtained.

EXAMPLE 9

A 2-liter 3-necked flask was equipped with stirrer, thermometer and a 30 cm column of filling bodies (Raschig rings). The heat of the column was connected to a 500 ml receiver through a distillation bridge. The apparatus was attached to a water jet pump through a condensation trap cooled with carbon dioxide snow. 160 g (1 mol) of N,N-diethyl-N'-methoxymethyl-urea (purity <98%) and 504 g (3 mol) of hexamethylene diisocyanate were weighted into the reaction flask. A weighed quantity (ca 200 ml) of distilled chlorobenzene was introduced into the receiver which was then chilled with carbon dioxide snow. When the apparatus had been fully evacuated by the water jet pump, the reaction flask was heated rapidly to 100° C. and then slowly to 130° C. The reaction was stopped after 4 hours, the contents of the receiver were recovered after it had thawed to room temperature and the quantity of MMI solution in chlorobenzene was titrated to determine its isocyanate content (crude yields of MMI: 87% of the theoretical yield).

The solution in chlorobenzene was distilled over a 30 cm column of filling bodies (Raschig rings) at normal pressure and yielded virtually pure MMi (corresponding to the titrated isocyanate content). Pure yield: 80% of the theoretical yield (based on the quantity of urea put into the process).

EXAMPLE 10

A 2-liter 3-necked flask was equipped with stirrer, thermometer and a 30 cm column of filling bodies (Raschig rings). The head of the column was connected to a distillation bridge through a 500 ml receiver. The apparatus was attached to a water jet pump through a condensation trap cooled with carbon dioxide snow. 160 g (1 mol) of N,N-diethyl-N'-methoxymethyl-urea (purity <98%) and 168 g (1 mol) of hexamethylene diisocyanate were weighed into the reaction flask. A weighed quantity (ca. 200 ml) of distilled chlorobenzene was introduced into the receiver which was then chilled with carbon dioxide snow. When the apparatus had been fully evacuated by the water jet pump, the reaction flask was heated rapidly to 100° C. and then slowly to 130° C. The reaction was stopped after 3 hours, the contents of the receiver were recovered after thawing to room temperature and the solution of MMI in chlorobenzene obtained was titrated for its isocyanate content (crude yield of MMI: 78% of the theoretical yield).

The solution in chlorobenzene was distilled over a 30 cm of filling bodies (Raschig rings) at normal pressure and yielded virtually pure MMI (corresponding to the titrated isocyanate content) in an amount of 75% of the theoretical yield (based on the quantity of urea put into the process).

EXAMPLE 11

A 2-liter 3-necked flask was equipped with stirrer, thermometer and a 30 cm column of filling bodies (Raschig rings). The head of the column was connected to a 500 ml receiver through a distillation bridge. The apparatus was attached to a water jet pump through a condensation trap cooled with carbon dioxide snow. 320 g (2 mol) of N,N-diethyl-N'-methoxymethyl-urea (purity 98%) and 185 g (1.1 mol) of hexamethylene diisocyanate were weighed into the reaction flask. A weighed quantity (ca 200 ml) of distilled chlorobenzene was introduced into the receiver and chilled with carbon dioxide snow. When the apparatus had been fully evacuated by the water jet pump, the reaction flask was heated rapidly to 100° C. and then slowly to 150° C. The reaction was stopped after 2 hours, the contents of the receiver were recovered after thawing to room temperature and the solution of MMI in chlorobenzene obtained was titrated to determine its isocyanate content (crude yield of MMI: 74% of the theoretical yield).

The solution in chlorobenzene was distilled over a 30 cm column of filling bodies (Raschig rings) at normal pressure and yielded virtually pure MMI (corresponding to the titrated isocyanate content). Pure yield: 52% of the theoretical yield (based on the quantity of urea put into the process).

EXAMPLE 12

A 2-liter 3-necked flask was equipped with stirrer, thermometer and a 30 cm column of filling bodies (Raschig rings). The head of the column was connected to a 500 ml receiver through a distillation bridge. The apparatus was attached to a water jet pump through a condensation trap cooled with carbon dioxide snow. 216 g (1 mol) of N,N-di-n-butyl-N'-methoxymethyl-urea (purity 98%) and 168 g (1 mol) of hexamethylene diisocyanate were weighed into the reaction flask. A weighed quantity (ca 200 ml) of distilled chlorobenzene was introduced into the receiver and chilled with carbon dioxide snow. When the apparatus had been fully evacuated by the water jet pump, the reaction flask was heated rapidly to 100° C., then slowly to 150° C. The reaction was stopped after 2 hours, the contents of the receiver were recovered after thawing to room temperature and the solution of MMI in chlorobenzene obtained was titrated for its isocyanate content (crude yield of MMI: 84% of the theoretical yield).

The solution in chlorobenzene was distilled over a 30 cm column of filling bodies (Raschig rings) at normal pressure and yielded virtually pure MMI (corresponding to the titrated isocyanate content). Pure yield: 79% of the theoretical yield (based on the quantity of urea put into the process).

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of isocyanates corresponding to the following general formula:

R—O—CH$_2$—NCO, characterized in that tri-substituted ureas corresponding to the following general formula:

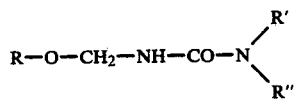

are reacted at temperatures of from about 50° to 250° C. with organic mono- or poly-isocyanates which have a boiling point above that of the product of the process, in which general formulae:

R represents a saturated aliphatic hydrocarbon group having from 1 to 4 carbon atoms or an allyl group; and R' and R" independently represent organic groups which are inert under the reaction conditions and the groups R' and R" may, together with the nitrogen atom of the urea group, from a heterocyclic ring.

2. The process according to claim 1, characterized in that the reaction is carried out in the presence of organic compounds which contain carbodiimide groups.

3. The process of claim 2, characterized in that instead of or in addition to the simultaneous use of higher boiling mono- or poly-isocyanates and organic compounds which contain carbodiimide groups there are used carbodiimide group-containing organic isocyanates which have a boiling point above the boiling point of the product of the process.

4. The process of claim 1, wherein said tri-substituted ureas have a purity of at least about 98% and no carbodiimide group containing compounds are present.

5. The process of claim 1, wherein said tri-substituted ureas have a purity of less than about 98% and between about 0.03 and 0.2 mol of carbodiimide groups are present per tri-substituted urea group

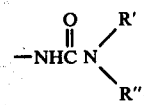

with R' and R" as defined in claim 1.

6. The process of claim 1, wherein between about 1 and 20 equivalents of isocyanate groups are present per mol of said tri-substituted urea.

7. The process of claim 1, wherein R is a methyl group.

8. The process of claim 1, wherein R' and R" are saturated or unsaturated C$_1$ to C$_6$ aliphatic hydrocarbon groups or form a saturated heterocyclic ring with the urea nitrogen to which they are attached.

* * * * *